US012193808B2

United States Patent
Uhlrich et al.

(10) Patent No.: US 12,193,808 B2
(45) Date of Patent: Jan. 14, 2025

(54) REAL-TIME ELECTROMYOGRAPHY FEEDBACK TO CHANGE MUSCLE ACTIVITY DURING COMPLEX MOVEMENTS

(71) Applicant: The Board of Trustees of the Leland Stanford Junior University, Stanford, CA (US)

(72) Inventors: Scott David Uhlrich, Stanford, CA (US); Scott L. Delp, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 50 days.

(21) Appl. No.: 17/257,708

(22) PCT Filed: Jul. 3, 2019

(86) PCT No.: PCT/US2019/040478
§ 371 (c)(1),
(2) Date: Jan. 4, 2021

(87) PCT Pub. No.: WO2020/010187
PCT Pub. Date: Jan. 9, 2020

(65) Prior Publication Data
US 2021/0290104 A1 Sep. 23, 2021

Related U.S. Application Data

(60) Provisional application No. 62/694,099, filed on Jul. 5, 2018.

(51) Int. Cl.
*A61B 5/11* (2006.01)
*A61B 5/00* (2006.01)
(Continued)

(52) U.S. Cl.
CPC ........ *A61B 5/112* (2013.01); *A61B 5/150809* (2013.01); *A61B 5/150816* (2013.01);
(Continued)

(58) Field of Classification Search
CPC ... A61B 5/112; A61B 5/389; A61B 5/150809; A61B 5/150816; A61B 5/150824;
(Continued)

(56) References Cited

U.S. PATENT DOCUMENTS 9,974,478 B1 * 5/2018 Brokaw ................. A61B 5/486
10,993,639 B2 * 5/2021 Herr ..................... A61B 5/4585
(Continued)

OTHER PUBLICATIONS

Ng et al. Biofeedback exercise improved the EMG activity ratio of the medial and lateral vasti muscles in subjects with patellofemoral pain syndrome. J Electromyogr Kinesiol. Feb. 2008;18(1):128-33.
(Continued)

*Primary Examiner* — Eric J Messersmith
*Assistant Examiner* — Chanel J Jhin
(74) *Attorney, Agent, or Firm* — LUMEN PATENT FIRM

(57) ABSTRACT

A training method is provided to train changing muscle contribution in a human subject while the human subject is performing a complex movement. Feedback is provided in a simple understandable fashion by one or more data points calculated based on electromyography signals obtained over e.g. a stance phase of a walking cycle. The training method showed a significantly increased training effect in subjects performing these complex movements where these subjects were able to change the muscle activation given a specific goal. The training could be setup of a single muscle or multiple muscles. The data point feedback could be a measure for the single muscle or some relative measure for the multiple muscles. The training method results in improved coordination strategies and could be useful for
(Continued)

retraining purposes as well as intervention methods for musculoskeletal pathologies or movement disorders.

5 Claims, 2 Drawing Sheets

(51) Int. Cl.
  *A61B 5/15* (2006.01)
  *A61B 5/389* (2021.01)
(52) U.S. Cl.
  CPC ........ *A61B 5/150824* (2013.01); *A61B 5/389* (2021.01); *A61B 5/486* (2013.01); *A61B 5/725* (2013.01)
(58) Field of Classification Search
  CPC ..... A61B 5/486; A61B 5/725; A61B 5/04012; A61B 5/0488; A61B 5/11; A61B 5/1107; A61B 5/1108; A61B 5/1114; A61B 5/224; A61B 5/4023; A61B 5/4519; A61B 5/6828; A63B 2230/605; A63B 2208/0204; A63B 2208/0209; A63B 24/0075; G01P 13/00

USPC .......................................................... 600/595
See application file for complete search history.

(56) References Cited

U.S. PATENT DOCUMENTS

| | | |
|---|---|---|
| 2011/0208444 A1 | 8/2011 | Solinsky |
| 2013/0310979 A1 | 11/2013 | Herr |
| 2014/0128939 A1* | 5/2014 | Embrey ............. A61N 1/36034 607/49 |
| 2016/0144226 A1 | 5/2016 | Artemiadis |
| 2017/0196483 A1* | 7/2017 | Bounyong ............. A61B 5/296 |

OTHER PUBLICATIONS

Huang et al. EMG biofeedback effectiveness to alter muscle activity pattern and scapular kinematics in subjects with and without shoulder impingement J. Electromyography & Kinesiology 23(1) Feb. 2013, pp. 267-274.

* cited by examiner

REAL-TIME ELECTROMYOGRAPHY FEEDBACK TO CHANGE MUSCLE ACTIVITY DURING COMPLEX MOVEMENTS

CROSS-REFERENCE TO RELATED APPLICATIONS

This application is a 371 of PCT application PCT/US2019/040478 filed Jul. 3, 2019. PCT application PCT/US2019/040478 claims the benefit of U.S. Provisional application 62/694,099 filed Jul. 5, 2018.

FIELD OF THE INVENTION

This invention relates to real-time electromyography feedback to change muscle activity in humans during complex movements.

BACKGROUND OF THE INVENTION

The human musculoskeletal system has dozens of joints that are over-actuated by redundant musculature; i.e. multiple muscles actuate to the same degree of freedom. Muscle redundancy provides the central nervous system with many possible coordination strategies to accomplish the same task. The central nervous system coordinates the activity of these muscles to achieve some objective such as walking in a way that minimizes energy expenditure. However, a particular coordination strategy for a task like walking may no longer be optimal as a result of injury, surgery, disease, or medical condition.

In the example of a walking cycle, knee joint forces could be too high as a result of increased gastrocnemius activity relative to soleus activity. In a training or rehabilitation protocol it might be desired to reduce the gastrocnemius activity relative to soleus activity and potentially increase soleus activity. As such, knee joint forces could then be lowered during the walking by reducing gastrocnemius activation and increasing soleus activation to produce the required plantarflexion moment.

Generally speaking, training to change the relative activation of redundant/synergistic muscles or antagonistic muscles could result in symptomatic improvements for these individuals. Changing which calf muscle is used during walking can reduce the forces in the knee joint by up to 50%. This reduction in joint force could improve their symptoms.

This invention advances the art with biofeedback technology with which humans are able to change muscle activity in real-time during complex movements such as walking.

SUMMARY OF THE INVENTION

A training method is provided for changing relative muscle contribution in a human subject while the human subject is performing a complex movement. A complex movement is defined as a movement that distinguishes a stance phase where a leg is in contact with a surface followed by a swing phase where the leg is swinging through air and is not in contact with the surface. The leg cycles through a sequence of stance phases and swing phases during the complex movement. Examples of complex movements in the spirit of this invention are walking, running, navigating stairs (ascending/descending), or other movements in the spirit of the invention such as hopping, cutting, jumping where there is a repetitive component of the leg or arm executing these movements. Further in the same spirit of the invention, complex movements could also be defined as ambulatory movements. Key is that the movements/motions of this invention are not static exercises.

In a first embodiment of the training method, a human subject performs a complex movement (FIG. 1). Electromyography (EMG) is recorded from a first muscle and a second muscle over a first stance phase, which are then both processed. In one example, the recorded EMGs are processed by applying a bandpass filter, rectifying the EMG signals, and then lowpass filtering the EMGs to create linear envelopes for the first muscle and the second muscle (FIG. 2). The linear envelops could also be normalized to an electromyography standard, e.g. a sub-maximal activity or maximum-effort activity. In one example, EMG obtained while jumping as high as possible could serve for normalization.

A data point is calculated for the first stance phase. This data point represents a relative muscle contribution of the first muscle and the second muscle over the first stance phase. In one example the data point could be the activation ratio between the first and second muscle. In another example, the data point could be the average of the processed EMG of either the first or the second muscle. In any case, the data point is calculated using the recorded and processed electromyography of both the first muscle and the second muscle over the first stance phase. Other examples in the spirit of the invention for data points to be calculated are the mean of the linear envelope, the root-mean-square (RMS) of the linear envelope, or the peak/maximum of the linear envelope. Further in the spirit of the invention the electromyography could be fed into a model of nonlinear muscle dynamics to estimate muscle force or even a musculoskeletal model. Date points of the estimated muscle could then be used as feedback. Estimated muscle force could also be translated into an estimated contribution of a given muscle's force on a parameter of interest such as joint contact loading.

The calculating step occurs during the first swing phase immediately after the completion of the first stance phase and prior to the start of a subsequent stance phase immediately following the first swing phase. The subsequent stance phase could be the one immediately following stance phase for the same leg, or the one at a later stance phase during the movement cycle.

The training method then provides feedback of the data point to the human subject performing the complex movement during the first swing phase and prior to the start of the subsequent stance phase immediately following the first swing phase. In one example, just a single data point is fed back to the human subject. In another example, two data points could be fed back to the human subject. In yet another example, the feedback could be defined as step-by-step feedback, but it could also be feedback that is averaged after a two or more steps.

The feedback is intended for the human subject to change the relative muscle contribution of the first muscle and the second muscle in the subsequent stance phase. The feedback of the data point can be given in the form of a visual, auditory, or tactile cue. In any case, the feedback has to be informative to the human subject whether to increase or decrease the first muscle activation relative to the second muscle activation, or vice versa, during the subsequent stance phase.

In the training method, the human subject is given a goal to change the data point(s) by changing the first muscle activation relative to the second muscle activation, or vice versa. In one example, the human subject is not given a goal to change kinematics of the complex movement. In another example, the human subject is given a goal to maintain kinematics of the complex movement. In yet another example, it is conceivable that a change in kinematics may also be beneficial.

The recording, processing and feedback is accomplished by a computer processor capable of receiving the electromyography from the first and second muscle, capable of processing the received electromyography from the first and second muscle, capable of calculating the data point(s) based on the processed electromyography from the first and second muscle, and capable of providing the feedback to the human subject. One can envision mobile solutions and implementations of the processing steps and feedback.

In a second embodiment of the training method, similar to the spirit of the first embodiment and as alluded to infra, the training method could focus on recording electromyography of a single muscle and the data point is calculated for that single muscle.

The technology developed herein is the use of real-time feedback (rather than off-line analysis) on muscles to train a person to use alternate/redundant muscles based on just a single data point reflecting an entire stance phase. Embodiments have the following advantages over existing approaches:

Understandable feedback: In this invention EMG is processed and presents one or two data points of understandable feedback at an actionable frequency (e.g. the sum of the ratio of processed muscle activations during a critical part of the gait cycle was presented one time per walking cycle). Prior work displayed the continuous signal of EMG signals from multiple muscles simultaneously, asking patients to change the ratio between these signals. The inventors of this application found such a method to be very challenging to interpret during complex motor tasks such as walking.

Activation Ratio Change without Kinematic Instructions: Prior work has achieved changes in activation patterns by suggesting kinematic changes. One example of prior work suggests performing an exercise tasks using different hip and knee angles. In many cases like altering joint loading, it is preferable to simply alter the muscle activation patterns without changing the movement dynamics. The feedback provided as proposed in this invention was simple enough that participants have been able to change their activations without dramatic changes in kinematics.

Rate of motor learning: The nature of our feedback facilitates remarkably fast motor learning. This was perhaps the most surprising finding. Prior works by other reported for example a 24% change in activation ratio for the biofeedback group compared to control after 8 weeks of 30 minutes of daily training. The training method provided in this application observed a 24% change in activation ratio during walking after 5 minutes of biofeedback. Furthermore, the inventors of this invention have also demonstrated that participants were able to retain what was taught, based on the training method provided herein, after the feedback was removed. In one experiment, subjects were only given three 5-minute feedback trials before assessing retention on the same day. Such retention suggests that the motor pattern became recognizable and controllable without the presence of feedback after only a short epoch of training.

Carry-over of training effect: The training method of the invention provides understandable feedback combined with the increased rate of motor learning. Prior work gave feedback of several continuous signals during controlled (simple and/or static) movements in the hope it would translate into more complex activities of daily living where the activations are actually important like walking and stair navigation. The feedback proposed in this invention is understandable enough that it can be given and acted upon in the midst of the actual dynamic activities that we care about such as walking, running, cutting, jumping.

DETAILED DESCRIPTION

The example provided herein pertain to walking which is based on a study to understand the feasibility whether humans have the ability of conscious control over individual muscles in real-time during complex movements such as walking to be able to make these changes that could improve their mobility. As a skilled artisan would readily understand, this example can be extended to other complex movements.

Methods

Figure 1:
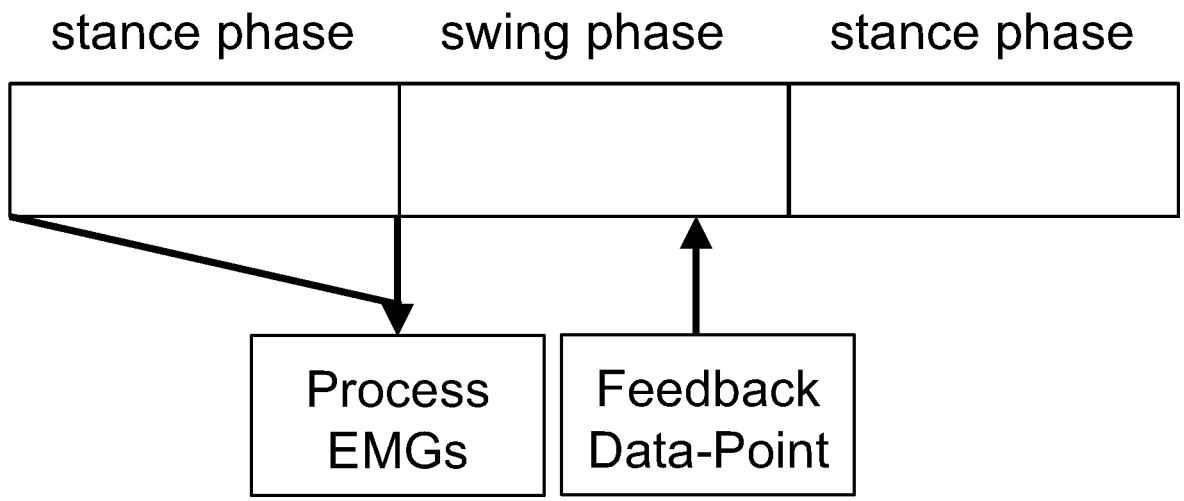
FIG. 1 shows a training method according to an exemplary embodiment of the invention.
Figure 2:
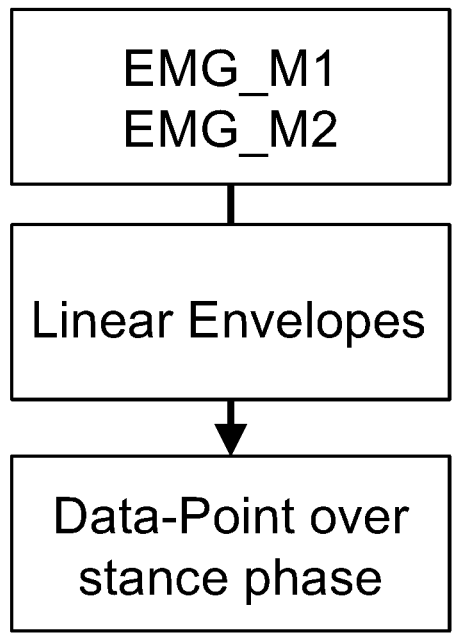
FIG. 2 shows EMG processing according to an exemplary embodiment of the invention.
Figure 3B:
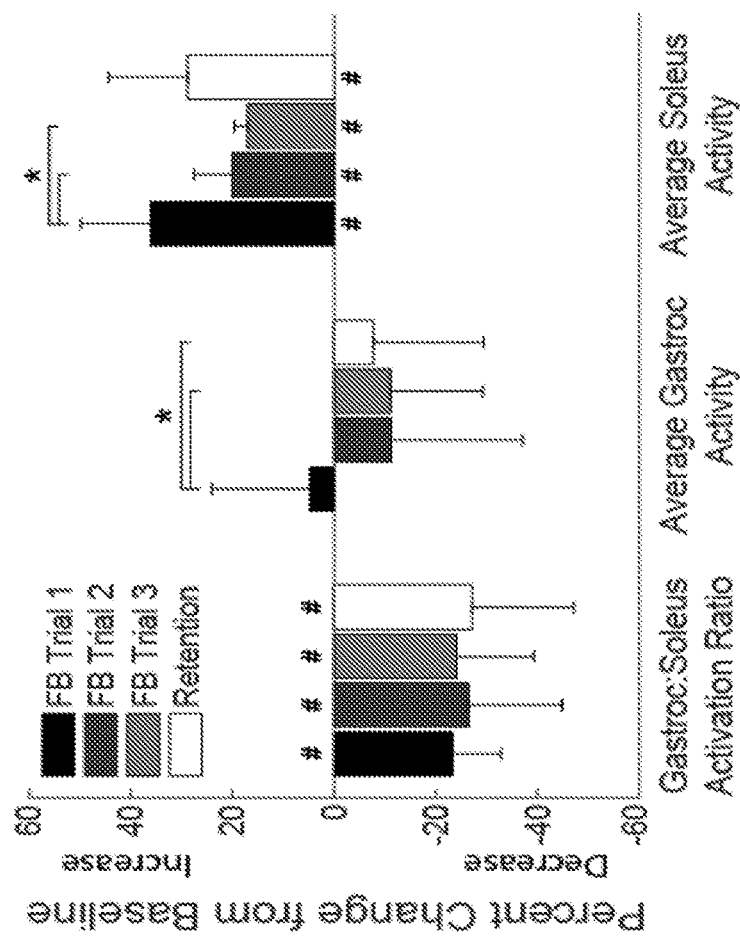
FIGS. 3A-B show according to an exemplary embodiment of the invention representative real-time feedback from the second and third feedback (FB) trials (FIG. 3A). Percent changes in activation ratio and stance-phase-averaged muscle activity from baseline (FIG. 3B). ($p<0.05$: # different than 0, * different than first feedback trial)
Figure 3A:
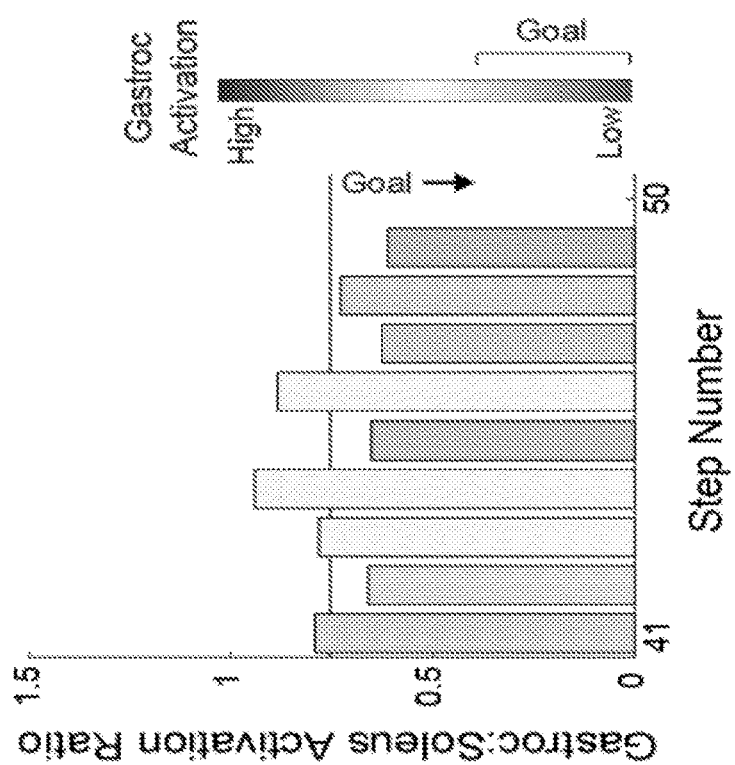

Medial gastrocnemius and soleus electromyograms were recorded from 5 healthy adults walking on a treadmill. The gastrocnemius-to-soleus activation ratio was computed after each step by dividing the gastrocnemius by soleus stance-phase-averaged electromyogram linear envelope. Subjects performed a 1-minute baseline trial followed by three 6-minute feedback trials. In the first feedback trial, subjects were asked to reduce their activation ratio which was displayed as a real-time bar plot. During the second and third feedback trials, the bars were colored according to gastrocnemius activation (FIG. 3A), encouraging subjects to reduce their activation ratio by decreasing gastrocnemius activity. For the first four minutes of each feedback trial, subjects were instructed to explore different strategies to change their activation without changing their kinematics. They were then asked to walk consistently with their best strategy during the final 2 minutes of each trial. Following the 3 feedback trials, subjects performed a 6-minute retention trial without feedback. The final 30 steps of each trial were analyzed and compared with t-tests ($\alpha=0.05$).

Results

Compared to baseline, the gastrocnemius-to-soleus activation ratio decreased during all trials by 24-27% ($p<0.05$). During the first feedback trial, when only activation ratio was displayed, subjects reduced their activation ratio ($p=0.005$) compared to baseline by increasing soleus activity ($p=0.004$). During the third feedback trial, when activation ratio and gastrocnemius activation were displayed, subjects decreased gastrocnemius ($p=0.033$) activity compared to the first feedback trial, but showed no further reduction in activation ratio ($p=0.882$, FIG. 3B).

Based on these results, human subjects were able to voluntarily modulate redundant muscle activation during walking with real-time visual feedback. Improved coordination strategies emerged when subjects were shown gastrocnemius activation and activation ratio, compared to activation ratio alone. Coordination retraining, as we have performed here, could become a promising intervention for musculoskeletal pathologies.

Applications of embodiments of the invention could be relative muscle activation feedback for movement disorders. Clinical benefits of the present invention are:

Osteoarthritis: The field has sought to reduce joint loading with bracing and by drastically changing the way that people move their limbs while walking. Patients are often non-compliant with these interventions due to the stigma of walking awkwardly or wearing a cumbersome brace. After learning a modified muscle coordination strategy from our device, individuals can walk without any visible changes, but be achieving a similar joint load reduction. Additionally, our device could be coupled with the standard of care to achieve additional reduction in joint loading.

Patellofemoral Pain and Stroke: The standard of care is clinic-based therapy which works on strengthening, active range of motion, and performing functional movements. These protocols are often ineffective at altering the underlying muscle coordination deficiencies. By directly measuring and giving feedback on the relative activity of involved muscles, patients may be able to alter their coordination strategies, thus improving mobility and symptoms.

What is claimed is:

1. A training method of changing relative muscle contribution in a human subject while the human subject is performing a complex movement, comprising:
   (a) the human subject executing the complex movement, wherein the executing complex movement distinguishes a stance phase where a leg is in contact with a surface followed by a swing phase where the leg is swinging through air and is not in contact with the surface, and
      wherein during the performing complex movement the leg cycles through a sequence of stance phases and swing phases;
   (b) placing a first electrode over a first muscle of the human subject wherein the first muscle is a gastrocnemius, and through the first electrode computer recording a first time-series of electromyography from the first muscle over a first stance phase, and computer processing the recorded electromyography from the first muscle;
   (c) placing a second electrode over a second muscle of the human subject wherein the second muscle is a soleus of the same leg of the human subject, wherein the first muscle and the second muscle are synergistic muscles to each other, and through the second electrode computer recording a second time-series of electromyography from the second muscle over the first stance phase, and computer processing the recorded electromyography from the second muscle, wherein the computer processing of the computer recorded electromyography through the first electrode and the second electrode comprises applying a bandpass filter, rectifying the electromyography, applying a lowpass filtering to create a linear envelope for the first muscle and a linear envelope for the second muscle, and normalizing the electromyography for the first muscle and for the second muscle to an electromyography standard;
   (d) computer determining a data point for the first stance phase,
      wherein the data point is determined as a relative muscle contribution of the processed first muscle electromyography and the processed second muscle electromyography over the first stance phase, and
      wherein the determining step occurs during the first swing phase immediately after a completion of the first stance phase and prior to a start of a subsequent stance phase immediately following the first swing phase; and
   (e) providing feedback of the computer determined data point to the human subject performing the complex movement during the first swing phase and prior to the start of the subsequent stance phase immediately following the first swing phase,
      wherein the human subject uses the computer determined data point as feedback to change the relative muscle contribution of the first muscle and the second muscle in the subsequent stance phase,
      wherein the feedback of the data point is in the form of a visual, auditory, or tactile cue, and
      wherein the feedback is informative to the human subject whether to increase or decrease activation of the first muscle relative to activation of the second muscle, or vice versa, during the subsequent stance phase.

2. The method as set forth in claim 1, wherein further comprising calculating another data point for the first stance phase, and providing feedback of the other data point to the human subject performing the complex movement during the first swing phase and prior to the start of the subsequent stance phase immediately following the first swing phase.

3. The method as set forth in claim 1, wherein the human subject is given a goal to change the data point by changing the first muscle activation relative to the second muscle activation, or vice versa.

4. The method as set forth in claim 1, wherein the human subject is not given a goal to change kinematics of the complex movement.

5. The method as set forth in claim 1, wherein the human subject is given a goal to maintain kinematics of the complex movement.

* * * * *